United States Patent
Lao et al.

(10) Patent No.: US 8,487,085 B2
(45) Date of Patent: Jul. 16, 2013

(54) ANALYZING MESSENGER RNA AND MICRO RNA IN THE SAME REACTION MIXTURE

(75) Inventors: Kai Lao, Pleasanton, CA (US); Neil Straus, Emeryville, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 212 days.

(21) Appl. No.: 12/781,690

(22) Filed: May 17, 2010

(65) Prior Publication Data

US 2010/0221790 A1 Sep. 2, 2010

Related U.S. Application Data

(63) Continuation of application No. 11/458,089, filed on Jul. 17, 2006, now Pat. No. 7,745,122.

(60) Provisional application No. 60/699,930, filed on Jul. 15, 2005.

(51) Int. Cl.
*C07H 21/02* (2006.01)
*C07H 21/04* (2006.01)
*C12N 9/00* (2006.01)

(52) U.S. Cl.
USPC .......................... 536/23.1; 536/24.3; 435/183

(58) Field of Classification Search
None
See application file for complete search history.

(56) References Cited

U.S. PATENT DOCUMENTS

| | | | |
|---|---|---|---|
| 5,234,809 A | 8/1993 | Boom et al. | |
| 5,338,671 A | 8/1994 | Scalice et al. | |
| 5,411,876 A | 5/1995 | Bloch et al. | |
| 5,677,152 A | 10/1997 | Birch et al. | |
| 5,773,258 A | 6/1998 | Birch et al. | |
| 6,605,451 B1 | 8/2003 | Marmaro et al. | |
| 7,575,863 B2 | 8/2009 | Chen et al. | |
| 7,601,495 B2 | 10/2009 | Chen et al. | |
| 7,601,821 B2 | 10/2009 | Anderson et al. | |
| 7,604,937 B2 | 10/2009 | Lao et al. | |
| 7,745,122 B2 | 6/2010 | Lao et al. | |
| 2005/0042666 A1 | 2/2005 | Nazarenko et al. | |
| 2005/0272075 A1 | 12/2005 | Jacobsen et al. | |
| 2006/0057595 A1 | 3/2006 | Lao et al. | |
| 2006/0078906 A1 | 4/2006 | Chen et al. | |
| 2006/0223066 A1 | 10/2006 | Lao et al. | |
| 2006/0269943 A1 | 11/2006 | Bloch | |
| 2007/0015176 A1 | 1/2007 | Lao et al. | |
| 2007/0015187 A1 | 1/2007 | Lao et al. | |
| 2007/0048757 A1 | 3/2007 | Lao et al. | |
| 2007/0059739 A1 | 3/2007 | Lao | |
| 2007/0077570 A1 | 4/2007 | Lao et al. | |
| 2007/0128620 A1 | 6/2007 | Lao et al. | |

FOREIGN PATENT DOCUMENTS

| | | |
|---|---|---|
| WO | WO-98/22489 | 5/1998 |
| WO | WO-99/14226 | 3/1999 |
| WO | WO-00/39352 | 7/2000 |
| WO | WO-2004/051218 | 6/2004 |

OTHER PUBLICATIONS

Ailenberg, M. "Controlled Hot Start and Improved Specificity in Carrying Out PCR Utilizing Touch Up and Loop Incorporated Primers (TULIPS)" Biotechniques 29 Eaton Publishing Co. (minus advertisement pages) 2000, pp. 1018-1024.

Fujimori, Shizuyoshi "Enantio-DNA Recognizes Complimentary RNA but Not Complementary DNA", J. Am. Chem. Soc., vol. 112 1990, pp. 7436-7438.

Garbesi, Anna "L-DNAs as potential antimessenger oligonucleotides: a reassessment", Nucleic Acids Research, vol. 21(18) 1993, pp. 4159-4165.

Ke, S.H. "Rapid and efficient site-directed mutagenesis by single-tube megaprimer PCR method", Nucleic Acids Research, vol. 25(16) 1997, pp. 3371-3372.

Mohamed, Nahla "A Sensitive and quantitative single-tube real-time reverse transcriptase-PCR for detection of enteroviral RNA", Journal of Clinical Virology, vol. 30 (2003), pp. 150-156.

Urata, Hidehito "Spectroscopic Characterization of Heterochiral DNAs", Nucleic Acids Symposium Series, No. 29, 1993, pp. 69-70.

Wetmur, James G. "Nucleic Acid Hybrids, Formation and Structure of", Molecular Biology and Biotechnology: A Comprehensive Desk Reference VCH Publishers, Inc., Robert A. Meyers, ed., 1995, pp. 605-608.

*Primary Examiner* — Kenneth R. Horlick
*Assistant Examiner* — David Thomas

(57) ABSTRACT

The present teachings provide methods, compositions, and kits for performing primer extension reactions on at least two target polynucleotides in the same reaction mixture. In some embodiments, a reverse transcription reaction is performed on a first target polynucleotide with a hot start primer comprising a self-complementary stem and a loop, and extension products form at high temperatures but extension products form less so at low temperatures since the self-complementary stem of the hot start primer prevents hybridization of the target specific region to the target. However, non-hot start primers with free target specific regions can hybridize to their corresponding targets at the low temperature and extension can happen at the low temperature.

11 Claims, 1 Drawing Sheet

ANALYZING MESSENGER RNA AND MICRO RNA IN THE SAME REACTION MIXTURE

CROSS-REFERENCE TO RELATED APPLICATIONS

Figure 1A:
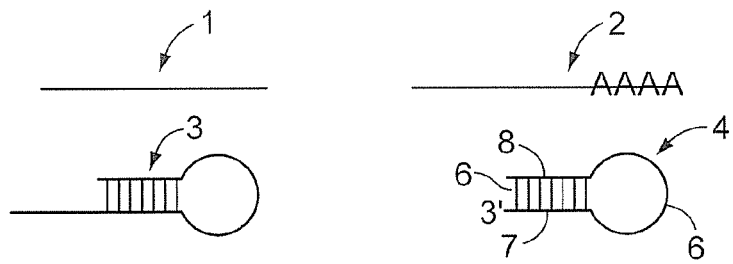

This application is a continuation of U.S. patent application Ser. No. 11/458,089 filed Jul. 17, 2006, now U.S. Pat. No. 7,745,122 B2, which claims a priority benefit under 35 U.S.C. §119(e) from U.S. Application No. 60/669,930 filed Jul. 15, 2005, the contents of which is incorporated herein by reference in their entireties.

FIELD

The present teachings relate to primer-extension mediated methods of synthesizing nucleic acids.

INTRODUCTION

The integrity of primer-mediated methods of synthesizing nucleic acids can be compromised by non-specific hybridization of primer to inappropriate target polynucleotides. The analysis of nucleic acids is benefited by approaches that minimize the generation of mis-extension products. For example, 'hot-start' approaches have been employed in PCR, where inhibition of polymerase activity has been achieved. For example, U.S. Pat. No. 5,338,671 describes the use of antibodies specific for a thermostable DNA polymerase to inhibit the DNA polymerase activity at low temperatures. Chemical treatment with citraconic anhydride is another way hot-start PCR has been achieved (see U.S. Pat. No. 5,773,258 and U.S. Pat. No. 5,677,152). Hot-start methods which use a heat labile material, such as wax, to separate or sequester reaction components are described in U.S. Pat. No. 5,411,876. The application of such hot-start approaches to reverse transcription have proven challenging. For example, many reverse transcriptases are not heat-stabile.

Analysis of expressed nucleic acids can be difficult in small and limited samples. Approaches that multiplex nucleic acid analyses are of growing importance in the biomedical research community.

SUMMARY

In some embodiments, the present teachings provide a method of forming a messenger RNA (mRNA) primer extension product and a micro RNA primer extension product in the same reaction mixture comprising; forming a reverse transcription reaction mixture comprising a hot start mRNA primer, a micro RNA primer, a target mRNA, a target micro RNA, and a reverse transcribing enzyme, wherein the hot start mRNA primer comprises a blunt-ended self-complementary stem and a loop, wherein the blunt-ended self-complementary stem comprises a target specific region and a quencher region; hybridizing the micro RNA primer to the target micro RNA at a low temperature; extending the micro RNA primer at the low temperature to form a micro RNA extension product, wherein the self-complementary stem of the mRNA primer is substantially non-denatured; raising the temperature to a high temperature, wherein the self-complementary stem of the hot start mRNA primer is substantially denatured; hybridizing the target specific region of the hot start mRNA primer to the target mRNA at the high temperature; extending the hot start mRNA primer at the high temperature to form a mRNA extension product; and, forming the mRNA primer extension product and the micro RNA primer extension product in the same reaction mixture.

In some embodiments, the present teachings provide a method of forming a first primer extension product and a second primer extension product in the same reaction mixture comprising; forming a primer extension reaction mixture comprising a first primer, a hot start second primer, a first target, a second target, and a primer extending enzyme, wherein the hot start second primer comprises a blunt-ended self-complementary stem and a loop, wherein the blunt-ended self-complementary stem comprises a target specific region and a quencher region; hybridizing the first primer to the first target at a low temperature; extending the first primer at the low temperature to form a first primer extension product, wherein the self-complementary stem of the hot start second primer is substantially non-denatured; raising the temperature to a high temperature, wherein the self-complementary stem of the hot start second primer is substantially denatured; hybridizing the target specific region of the hot start second primer to the second target at the high temperature; extending the hot start second primer at the high temperature to form a second target extension product; and, forming the first primer extension product and the second primer extension product in the same reaction mixture.

In some embodiments, the present teachings provide a reaction mixture comprising a hot start mRNA primer, a micro RNA primer, a target mRNA, a target micro RNA, and a reverse transcribing enzyme, wherein the hot start mRNA primer comprises a blunt-ended self-complementary stem and a loop, wherein the blunt-ended self-complementary stem comprises a target specific region and a quencher region, wherein the self-complementary stem of the hot start mRNA primer is substantially non-denatured at a low temperature, and wherein the self-complementary stem of the hot start mRNA primer is substantially denatured at a high temperature.

In some embodiments, the present teachings provide a reaction mixture comprising a hot start mRNA primer, a micro RNA primer, a target mRNA, a target micro RNA and a reverse transcribing enzyme, wherein the hot start mRNA primer comprises a blunt-ended self-complementary stem and a loop, wherein the blunt-ended self-complementary stem comprises a target specific region and a quencher region, wherein the self-complementary stem of the hot start mRNA primer is non-denatured at a low temperature, and wherein the self-complementary stem of the hot start mRNA primer is denatured at a high temperature In some embodiments, the present teachings provide a kit for forming a messenger RNA (mRNA) primer extension product and a micro RNA (miRNA) primer extension product in the same reaction mixture comprising; a hot start mRNA primer, a micro RNA primer, and optionally a reverse transcribing enzyme, wherein the hot start mRNA primer comprises a blunt-ended self-complementary stem and a loop, wherein the blunt-ended self-complementary stem comprises a target specific region and a quencher region, wherein the self-complementary stem is substantially non-denatured at a low temperature, wherein the low temperature is less than 27 C, and wherein the self-complementary stem is substantially denatured at a high temperature, wherein the high temperature is between 35 C-60 C.

These and other features of the present teachings are set forth herein.

DRAWINGS

Figure 1B:
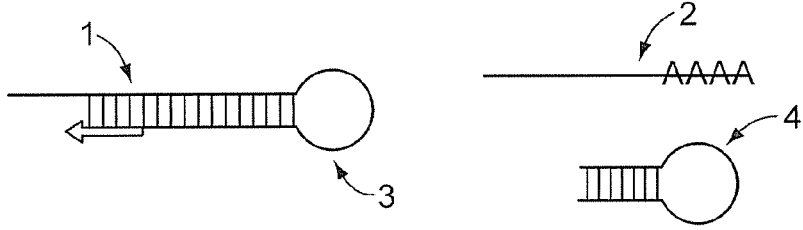
Figure 1C:
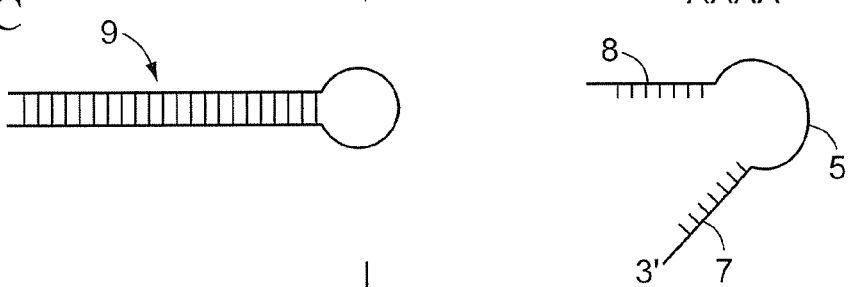
Figure 1D:
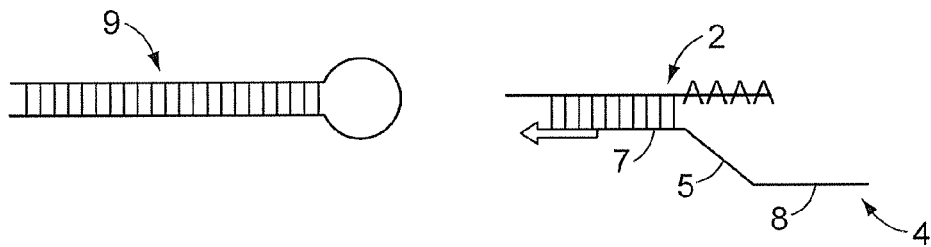

FIG. 1 depicts one illustrative embodiment according to the present teachings.

DESCRIPTION OF EXEMPLARY EMBODIMENTS

It is to be understood that both the foregoing general description and the following detailed description are exemplary and explanatory only and are not intended to limit the scope of the current teachings. In this application, the use of the singular includes the plural unless specifically stated otherwise. For example, "a forward primer" means that more than one forward primer can be present; for example, one or more copies of a particular forward primer species, as well as one or more different forward primer species. Also, the use of "comprise", "contain", and "include", or modifications of those root words, for example but not limited to, "comprises", "contained", and "including", are not intended to be limiting. The term and/or means that the terms before and after can be taken together or separately. For illustration purposes, but not as a limitation, "X and/or Y" can mean "X" or "Y" or "X and Y".

The section headings used herein are for organizational purposes only and are not to be construed as limiting the described subject matter in any way. All literature and similar materials cited in this application, including, patents, patent applications, articles, books, treatises, and internet web pages are expressly incorporated by reference in their entirety for any purpose. In the event that one or more of the incorporated literature and similar defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

SOME DEFINITIONS

As used herein, the term "hot start primer" refers to a primer comprising a self-complementary stem and a loop, wherein the self-complementary stem comprises a target specific region and a quencher region. At low temperatures, the target-specific region is hybridized to the quencher region. At high temperatures, the target-specific region is not hybridized to the quencher region, and can hybridize to the corresponding target polynucleotide, thereby allowing for a hot-start extension reaction. In some embodiments, the self-complementary stem is blunt-ended, such that there is not a nucleotide overlap at the 5' or 3' end of the self-complementary stem. In some embodiments, the mRNA primer comprises a nearly blunt-ended self-complementary stem, such as for example a single 3' nucleotide overhang. Generally, such 3' overhangs will be of minimal length to avoid undesired priming on targets prior to the melting of the self-complementary stem region by the high temperature. Overhangs on the 5' end are generally more tolerable, since extension does not proceed from the 5' of a sequence.

As used herein, the term "pre-amplifying" refers to a process wherein a multiplexed PCR is performed, followed by a plurality of lower-plex decoding PCRs. Typically the primers employed in the multiplexed PCR correspond to the primers employed in the plurality of lower-plex decoding PCRs. Illustrative teachings of such approaches can be found in WO2004/051218 to Andersen and Ruff, U.S. Pat. No. 6,605,451 to Xtrana, and U.S. Non-Provisional application Ser. No. 11/090,830 to Andersen et al., and U.S. Non-Provisional application Ser. No. 11/090,468 to Lao et al., As used herein, the term "denaturing" refers to the melting of two complementary nucleic acid strands, and is typically achieved by elevating the temperature. In some embodiments, denaturing can be achieved by the addition of base (e.g. —NaOH) or other approaches for dissociating nucleic acids that are familiar to one of ordinary skill in the art of molecular biology.

As used herein, the term "complementary" refers to nucleic acid sequences that are capable of forming Watson-Crick base-pairs. For example, a self-complementary primer comprises a self-complementary stem which is capable of forming Watson-Crick base-pairs with itself at a low temperature. When at the low temperature, the strands of such a self-complementary stem are said to be hybridized to one another. When at a high temperature, the strands of such a self-complementary stem are not hybridized to each other, and the target specific region of the self-complementary stem can be hybridized with a target. In this application, a statement that one sequence is complementary to another sequence encompasses situations in which the two sequences have slight mismatches. Here, the term "sequence" encompasses, but is not limited to, nucleic acid sequences, polynucleotides, oligonucleotides, probes, primers, primer-specific regions, and target-specific regions. Despite the mismatches, the two sequences should selectively hybridize to one another under appropriate conditions.

As used herein, the term "blunt-ended self-complementary stem" refers to an aspect of a hot start primer that is double-stranded and hybridizes to itself at a low temperature. In some embodiments, the stem is blunt-ended, in that there are not any overlapping, non-hybridized nucleotides, at the end of the hot start primer when the rest of the nucleotides in the stem are hybridized in base-pairs. In some embodiments, the stem has one, or two, or as many as three overlapping nucleotides, and possibly more, but for the purposes of the present teachings such a molecule can still be considered "blunt-ended." Thus, small overlaps, which are not expected to prime extension of a target when the rest of the stem is double-stranded, are within the scope of blunt-ended self-complementary stems of the hot start primers provided by the present teachings.

As used herein, the term "target polynucleotide" refers to a polynucleotide sequence that is sought to be reverse transcribed. The target polynucleotide can be obtained from any source, and can comprise any number of different compositional components. For example, the target can be nucleic acid (e.g. DNA or RNA), transfer RNA, siRNA, and can comprise nucleic acid analogs or other nucleic acid mimic, though typically the target will be messenger RNA (mRNA) and/or micro RNA (miRNA). The target can be methylated, non-methylated, or both. The target can be bisulfite-treated and non-methylated cytosines converted to uracil. Further, it will be appreciated that "target polynucleotide" can refer to the target polynucleotide itself, as well as surrogates thereof, for example amplification products, and native sequences. In some embodiments, the target polynucleotide is a short DNA molecule derived from a degraded source, such as can be found in for example but not limited to forensics samples (see for example Butler, 2001, *Forensic DNA Typing: Biology and Technology Behind STR Markers*. The target polynucleotides of the present teachings can be derived from any of a number of sources, including without limitation, viruses, prokaryotes, eukaryotes, for example but not limited to plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells, and lysed cells. It will be appreciated that target polynucleotides can be isolated from samples using any of a variety of procedures known in the art, for example the Applied Biosystems ABI Prism™ 6100 Nucleic Acid PrepStation, and the ABI Prism™ 6700 Automated Nucleic Acid Workstation, Boom et al., U.S. Pat. No. 5,234,809, mirVana RNA isolation kit (Ambion), etc. It will be appreciated that target polynucleotides can be cut or sheared prior to analysis, including the use of such procedures as mechanical force, sonication, restriction endonuclease cleavage, or any method known in the art. In general, the target polynucleotides of the present teachings will be single stranded, though in some embodiments the target polynucleotide can be double stranded, and a single strand can result from denaturation.

As used herein, the term "nucleotide" refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is, independently H, C$_1$-C$_6$ alkyl or C$_5$-C$_{14}$ aryl. Exemplary riboses include, but are not limited to, 2'-(C1-C6)alkoxyribose, 2'-(C5-C14)aryloxyribose, 2',3'-dide-hydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352, and WO 99/14226). Exemplary LNA sugar analogs within a polynucleotide include, but are not limited to, the structures:

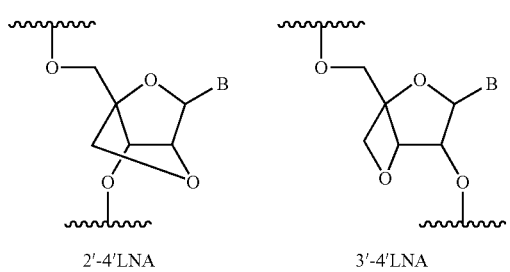

2'-4'LNA 3'-4'LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the N$^9$-position of the nucleotide base. When the nucleotide base is pyrimidine, e.g. C, T or U, the pentose sugar is attached to the N$^1$-position of the nucleotide base, except for pseudouridines, in which the pentose sugar is attached to the C5 position of the uracil nucleotide base (see, e.g., Kornberg and Baker, (1992) DNA Replication, 2$^{nd}$ Ed., Freeman, San Francisco, Calif.).

One or more of the pentose carbons of a nucleotide may be substituted with a phosphate ester having the formula:

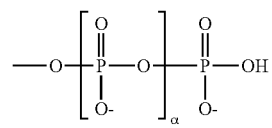

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see: Shabarova, Z. and Bogdanov, A. Advanced Organic Chemistry of Nucleic Acids, VCH, New York, 1994.

FIG. 1 depicts a method of forming a messenger RNA (mRNA) primer extension product and a micro RNA primer extension product in the same reaction mixture according to some embodiments of the present teachings.

In FIG. 1 (A), a reaction mixture is shown comprising a micro RNA target (1) a mRNA target (2), a micro RNA primer (3), and a mRNA primer (4), at a low temperature, for example 25 C room temperature. The mRNA primer (4) is a hot start primer, and comprises a loop (5) and a self-complementary stem (6), wherein the self complementary stem comprises a target specific region (7) and a quencher region (8). The 3' end of the target specific region (7) of the mRNA primer (4) is depicted. The poly-A tail at the 3' end of the mRNA target (2) is depicted as a series of A's.

In FIG. 1 (B), the micro RNA primer (3) hybridizes to the micro RNA target (1) and is extended (bold arrow), while the hot start mRNA primer (4) remains substantially non-denatured, and cannot hybridize to its corresponding mRNA target at the low temperature.

In FIG. 1 (C), the reaction mixture is heated to a high temperature, for example 42 C, and the hot start mRNA primer (4) is denatured, thus liberating the target-specific region (7) from the quencher region (8), with the loop (5) shown disposed therein. Also depicted in FIG. 1 (C) is the micro RNA extension product (9) and the target mRNA (2)

In FIG. 1 (D), the target specific region (7) of the hot start mRNA primer (4) is shown hybridized to the mRNA target (2) and is extended (bold arrow). The quencher region (8) and the loop (5) of the hot start mRNA primer, which are single-stranded, are also depicted.

In some embodiments, the architecture of the hot start primer can differ from that depicted in FIG. 1. For example, the loop (6) of the hot start primer shown in FIG. 1 can itself form part of the target-specific region of the hot start primer.

It will be appreciated that one of skill in the art would be able to make these and other minor modifications in the design of the hot start primer provided by the present teachings, and still be within their scope.

One of skill in the art will appreciate that the methods, compositions, and kits of the present teachings can be useful in a variety of contexts in which primer-extension on different target polynucleotides is desired to be performed in the same reaction mixture. In some embodiments of the present teachings, messenger RNA and micro RNA can be reverse transcribed using the methods of the present teachings. In some embodiments, the messenger RNA and micro RNA can be found in a small sample, for example a small sample derived from laser capture microdissection.

Certain methods of optimizing reverse transcription and amplification reactions are known to those skilled in the art. For example, it is known that PCR may be optimized by altering times and temperatures for annealing, polymerization, and denaturing, as well as changing the buffers, salts, and other reagents in the reaction composition. Optimization may also be affected by the design of the amplification primers used. For example, the length of the primers, as well as the G-C:A-T ratio may alter the efficiency of primer annealing, thus altering the amplification reaction. Descriptions of amplification optimization can be found in, among other places, James G. Wetmur, "Nucleic Acid Hybrids, Formation and Structure," in Molecular Biology and Biotechnology, pp. 605-8, (Robert A. Meyers ed., 1995); McPherson, particularly in Chapter 4; Rapley; and Protocols & Applications Guide, rev. 9/04, Promega.

In some embodiments, the present teachings contemplate single-tube RT-PCR approaches, and discussed for example in Mohamed et al., (2004) Journal of Clinical Virology, 30:150-156. In some embodiments, the reverse transcription products of the present teachings can be amplified in a multiplexed pre-amplifying PCR followed by a plurality of lower-plex decoding PCRs, as described for example in WO2004/051218 to Andersen and Ruff, U.S. Pat. No. 6,605, 451 to Xtrana, and U.S. Non-Provisional application Ser. No. 11/090,830 to Andersen et al., and U.S. Non-Provisional application Ser. No. 11/090,468 to Lao et al. Thus in some embodiments, the present teachings provide a method of quantifying a messenger RNA (mRNA) and a micro RNA from a small sample comprising; forming a reverse transcription reaction mixture comprising a hot start mRNA primer, a micro RNA primer, a target mRNA, a target micro RNA, and a reverse transcribing enzyme, wherein the hot start mRNA primer comprises a blunt-ended self-complementary stem and a loop, wherein the blunt-ended self-complementary stem comprises a target specific region and a quencher region; hybridizing the micro RNA primer to the target micro RNA at a low temperature; extending the micro RNA primer at the low temperature to form a micro RNA extension product, wherein the self-complementary stem of the hot start mRNA primer is substantially non-denatured; raising the temperature to a high temperature, wherein the self-complementary stem of the hot start mRNA primer is substantially denatured; hybridizing the target specific region of the hot start mRNA primer to the target mRNA at the high temperature; extending the hot start mRNA primer at the high temperature to form a mRNA extension product; forming the mRNA primer extension product and the micro RNA primer extension product in the same reaction mixture; pre-amplifying the mRNA primer extension product and the micro RNA primer extension product in a pre-amplification PCR; performing a first decoding PCR on the mRNA primer extension product and a second decoding PCR on the micro RNA primer extension product; and, quantifying the mRNA and the micro RNA from the small sample.

In some embodiments of the present teachings, a non hot-start primer can be employed that nonetheless comprises a self-complementary stem and a loop. Such primers will normally have a single-stranded target specific region that can hybridize to its corresponding target at a low temperature. Additional discussion of such primers can be found for example in U.S. Non-Provisional applications to Chen et al., Ser. No. 0/947,460 and Ser. No. 11/142,720. FIG. 1 depicts a scenario in which a non hot-start primer for a micro RNA target comprises a self-complementary stem, a loop, and single stranded target specific region, is present in a reaction mixture along with a hot start mRNA primer.

Generally, the length of the stem of the hot start primer can vary according to the context of the application. For example, when the target-specific region of the hot start primer is G:C rich, the length of the stem region can be shorter. Conversely, when the target-specific region of the hot start primer is A:T rich, the length of the stem region can be longer. Such procedures can be employed to adjust the length of the stem to correspond with a desired Tm, given a particular reaction context at hand. In some embodiments, the length of the stem is between 6-12 nucleotide base pairs.

Generally, the length of the loop of the hot-start primer will be between 8-24 nucleotides in length. Generally, short loops can have the beneficial effect of minimizing the likelihood of loop sequence displacing self-complementary stem duplex sequence at lower reaction temperatures. It will be appreciated by one of ordinary skill in the art that a variety of stem-loop configurations are available and within routine experimentation.

Illustrative molecular biology techniques of ready availability to one of skill in the art can be found in Sambrook et al., Molecular Cloning, 3rd Edition.

Certain Exemplary Kits

The instant teachings also provide kits designed to expedite performing certain of the disclosed methods. Kits may serve to expedite the performance of certain disclosed methods by assembling two or more components required for carrying out the methods. In certain embodiments, kits contain components in pre-measured unit amounts to minimize the need for measurements by end-users. In some embodiments, kits include instructions for performing one or more of the disclosed methods. Preferably, the kit components are optimized to operate in conjunction with one another.

Thus, in some embodiments the present teachings provide a kit for forming a messenger RNA (mRNA) primer extension product and a micro RNA (miRNA) primer extension product in the same reaction mixture comprising; a hot start mRNA primer, a micro RNA primer, and optionally a reverse transcribing enzyme, wherein the hot start mRNA primer comprises a blunt-ended self-complementary stem and a loop, wherein the blunt-ended self-complementary stem comprises a target specific region and a quencher region, wherein the self-complementary stem is non-denatured at a low temperature, wherein the low temperature is less than 27 C, and wherein the self-complementary stem is denatured at a high temperature, wherein the high temperature is between 35 C-60 C. In some embodiments, the micro RNA primer comprises a self-complementary stem, a loop, and a single-stranded target specific region, wherein the self-complementary stem is non-denatured at the low temperature.

Although the disclosed teachings have been described with reference to various applications, methods, and kits, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

We claim:

1. A reaction mixture comprising a hot start mRNA primer, a micro RNA primer, a target mRNA, a target micro RNA, and a reverse transcribing enzyme, wherein the hot start mRNA primer comprises a blunt-ended self-complementary stem and a loop, wherein the blunt-ended self-complementary stem comprises a target specific region and a quencher region, wherein the self-complementary stem of the hot start mRNA primer is capable of being non-denatured at a low temperature, and wherein the self-complementary stem of the hot start mRNA primer is capable of being denatured at a high temperature.

2. The reaction mixture according to claim 1 wherein the micro RNA primer comprises a self-complementary stem, a loop, and a single-stranded target specific region, wherein the self-complementary stem is substantially non-denatured at the low temperature.

3. The reaction mixture according to claim 2 wherein the self-complementary stem of the micro RNA primer is 6-12 nucleotide, base-pairs in length and the single-stranded target specific region is 6-8 nucleotides in length.

4. The reaction mixture according to claim 1 wherein the low temperature is 18 C-27 C.

5. A kit for forming a messenger RNA (mRNA) primer extension product and a micro RNA (miRNA) primer extension product in the same reaction mixture comprising;

a hot start mRNA primer, a micro RNA primer, and optionally a reverse transcribing enzyme, wherein the hot start mRNA primer comprises a blunt-ended self-complementary stem and a loop, wherein the blunt-ended self-complementary stem comprises a target specific region and a quencher region, wherein the self-complementary stem is non-denatured at a low temperature, wherein the low temperature is less than 27 C, and wherein the self-complementary stem is denatured at a high temperature, wherein the high temperature is between 35 C-60 C.

6. The kit according to claim 5 wherein the micro RNA primer comprises a self-complementary stem, a loop, and a single-stranded target specific region, wherein the self-complementary stem is non-denatured at the low temperature.

7. The reaction mixture according to claim 1 wherein the high temperature is 35 C-60 C.

8. The reaction mixture according to claim 1 wherein blunt-ended self-complementary stem comprises between 6 and 12 nucleotide base pairs in length.

9. The kit according to claim 5 wherein blunt-ended self-complementary stem comprises between 6 and 12 nucleotide base pairs in length.

10. The kit according to claim 5 wherein the micro RNA primer comprises a self-complementary stem, a loop, and a single-stranded target specific region, wherein the self-complementary stem is substantially non-denatured at the low temperature.

11. The kit according to claim 10 wherein the self-complementary stem of the micro RNA primer is 6-12 nucleotide base-pairs in length and the single-stranded target specific region is 6-8 nucleotides in length.

* * * * *